United States Patent [19]
Karpf et al.

[11] Patent Number: 5,228,350
[45] Date of Patent: Jul. 20, 1993

[54] METHOD FOR ANALYSING GASEOUS OR LIQUID SAMPLES AND A ONE-WAY MEASURING ELEMENT FOR USE IN SUCH A METHOD

[75] Inventors: Hellfried Karpf; Marcus J. Leiner; Anton Möstl, all of Graz; Klaus Reichenberger, Knittelfeld; Bernhard Schaffar; Werner E. Ziegler, both of Graz, all of Austria

[73] Assignee: AVL Medical Instruments AG, Schaffhausen, Switzerland

[21] Appl. No.: 643,273

[22] Filed: Jan. 22, 1991

[30] Foreign Application Priority Data

Jun. 8, 1990 [AT] Austria .................................. 1258/90

[51] Int. Cl.⁵ ...................... G01N 27/26; G01N 35/08
[52] U.S. Cl. ................................. 73/864.81; 204/409
[58] Field of Search .................. 73/864.81; 204/409, 204/410, 411, 229, 230, 275, 276, 277, 278

[56] References Cited

U.S. PATENT DOCUMENTS

| | | | |
|---|---|---|---|
| 3,976,450 | 8/1976 | Marcote et al. | 73/864.81 |
| 3,997,420 | 12/1976 | Buzza | 204/411 |
| 4,300,393 | 11/1981 | Stearns | 73/864.81 |
| 4,394,222 | 7/1983 | Rohr | 204/411 |
| 4,430,192 | 2/1984 | Maeda | 204/410 |
| 4,654,127 | 3/1987 | Baker et al. | |
| 4,734,184 | 3/1988 | Burleigh et al. | 204/409 |
| 4,840,074 | 6/1989 | Jessop | 73/864.81 |
| 4,871,439 | 10/1989 | Enzer et al. | 204/411 |
| 5,032,362 | 7/1991 | Marsoner et al. | 73/864.81 |
| 5,074,157 | 12/1991 | Marsoner et al. | 73/864.81 |

FOREIGN PATENT DOCUMENTS

| | | | |
|---|---|---|---|
| 0354895 | 2/1990 | European Pat. Off. | |
| 1260197 | 2/1968 | Fed. Rep. of Germany | 73/864.81 |
| 1245241 | 9/1971 | United Kingdom | 73/864.81 |

*Primary Examiner*—Hezron E. Williams
*Assistant Examiner*—George Dombroske
*Attorney, Agent, or Firm*—Watson, Cole, Grindle & Watson

[57] ABSTRACT

Method for analysing gaseous or liquid samples, utilising a one-way measuring element with a measuring channel containing at least one optical or electrochemical sensor and being provided with sealing elements on either end. In order to obtain accurate measurements in a simple manner the proposal is put forward that for measuring purposes a storage medium in the measuring channel be replaced by a separating medium which should then be replaced by the sample. Sample and storage medium will remain in the measuring element when it is discarded.

15 Claims, 8 Drawing Sheets

METHOD FOR ANALYSING GASEOUS OR LIQUID SAMPLES AND A ONE-WAY MEASURING ELEMENT FOR USE IN SUCH A METHOD

BACKGROUND OF THE INVENTION

This invention relates to a technique for analysing gaseous or liquid samples, utilising a one-way measuring element with a measuring channel containing at least one optical or electro- chemical sensor and being provided with sealing elements on either end.

DESCRIPTION OF THE PRIOR ART

A one-way measuring element for analysing gaseous or liquid samples is described in EP-A 354 895. This measuring element is provided with a measuring channel formed as a capillary tube containing optical sensors for sample analysis. Until the measuring element is used the measuring channel is sealed by a diaphragm on either end, and its interior is filled with a storage medium. Immediately before measurement the measuring element is calibrated, the storage medium also serving as a calibrating medium. Subsequently a diaphragm is perforated in the area of a sample-taking part, and the storage medium is displaced by the sample to be analysed.

Practical experience has shown that it is most difficult to find suitable media offering favorable characteristics both as storage and calibrating media. In this respect compromises must be made which could be avoided if separate media were used for storage and calibration.

In addition, the limited storage life of such measuring elements has proved a disadvantage, since the composition of the calibrating medium changes with the least diffusion. For this reason the measured results are no longer reliable when the measuring element is stored for a prolonged period of time.

Another measuring element is described in U.S. Pat. No. 4,654,127, which is provided with a measuring channel with several sensors. The inlet of the measuring channel can be connected to a vessel subdivided into two chambers, one of them containing a calibrating solution and the other one the sample to be analysed. Each chamber has an opening that is sealed with a pierceable diaphragm and may be put into contact with the inlet of the measuring channel.

After the sample has been introduced into the sample chamber the vessel is rotated from an initial position, in which none of the chambers communicate with the measuring channel, to a calibrating position, and the diaphragm sealing the calibrating chamber is perforated and the calibrating solution is drawn into the measuring zone by the capillary forces acting in the measuring channel, and is subsequently analysed. By further rotation of the vessel the sample chamber is put into contact with the inlet of the measuring channel and the sample is introduced into the measuring channel through the same opening after the diaphragm has been perforated, and is also analysed. The values obtained from the sample and calibrating liquids are used for determining the quantities to be measured in the sample.

The disadvantage of this type of measuring element is its complicated design. In blood gas analysis in particular, it is a disadvantage if the blood has to be fed from a sample-taking element, such as a syringe, into the sample chamber, from where it will enter the measuring channel only after further manipulation, since the blood gas values obtained may prove to be inaccurate because of the sample being exposed to ambient air, and reproducible results may be difficult to obtain. By effecting sample transport by means of capillary forces only, the calibrating solution cannot be reliably prevented from mixing with the sample, which may lead to measuring errors. In addition, infections of operating personnel due to the handling of contaminated blood samples cannot be excluded.

SUMMARY OF THE INVENTION

It is an object of the invention to avoid such disadvantages and to propose a highly accurate measuring technique, which is independent of the storage period of the measuring element and permits the use of a one-way measuring element of a simple design fit for mass-production.

It is a further object of the invention to propose a one-way measuring element with as short and direct a sample passage as possible between the point of sample withdrawal and the measuring zone in the measuring channel.

In the invention this object is achieved by providing that for measuring purposes a storage medium in the measuring channel be replaced by a separating medium, which should then be replaced by the sample. If sensors are used that do not need calibration, air or an inert gas may be used as a separating medium.

In all other instances it is proposed that the separating medium also be a calibrating medium. It is an advantage if the composition of the calibrating medium is different from that of the storage medium, the use of gases or gas mixtures being possible for calibrating the sensors, for instance, $CO_2$ or $O_2$ sensors.

As the individual filling and drainage processes are not only induced by the action of capillary forces but also by differential pressures applied by the analyser, the mixing of storage and calibrating media and the sample can largely be prevented. In this way accurate and reproducible measurement results are guaranteed.

In a preferred version it is provided that each medium be displaced by the one following it. In principle it is possible that the storage medium and/or calibrating medium be expelled from the measuring channel by blowing in air. This will not be necessary, however, if the storage medium is directly pushed out by the calibrating medium, and the latter directly by the sample. This is a particularly simple variant of the technique under discussion.

In a particularly hygienic and safe variant of the Method the openings of the measuring channel are sealed at the end of the measuring process, following which the measuring element is decoupled from the analyser and the sample-taking part, and is then discarded.

The invention also relates to a one-way measuring element for use in the above Method, comprising a measuring channel with at least one electrochemical or optical sensor located therein, a first opening on one end of the measuring channel for the connection of an analyser, a second opening on the other end of the measuring channel for the connection of a sample-taking part, and a first sealing element for the first opening as well as a second sealing element for the second opening.

It is provided by the invention that a collecting tank be located in the measuring element in the area of the second opening, and that the first sealing element have at least two positions, i.e., closing the measuring channel or connecting it to the first opening, and that the second sealing element have at least three positions, i.e., closing the measuring channel, connecting it to the collecting tank, or connecting it to the second opening.

The measuring element has a channel-shaped interior and an opening on each end designed to act as a coupling for connection of the analyser or the sample-taking part. Before the measuring process the two openings are kept sealed by the sealing elements and the measuring channel is filled with a storage liquid protecting the sensors from undesirable changes. After the analyser has been connected to the first opening, the first sealing element is actuated in order to establish a connection between the connecting line of the analyser and the measuring channel. At the same time the second sealing element is actuated to connect the measuring channel and the collecting tank. The sample-taking part may already be plugged into the second opening. By applying pressure to the analyser the storage medium may be pushed from the measuring channel into the collecting tank and a calibrating medium may be introduced into the measuring channel. In this state calibration is performed. As a calibrating medium a steam-saturated gas mixture may be used, containing $O_2$ at a partial pressure of 90 mm Hg, approximately, and $CO_2$ at 35 mm Hg, approximately, as well as an inert gas, preferably nitrogen. This will permit a two-point calibration at values closely approaching the physiological standard values.

If the second sealing element is brought into a third position, the measuring channel is connected to the sample-taking channel. By reversing the analyser the sample to be analysed, for instance, blood, can be sucked into the measuring channel. At the end of the measuring process both sealing elements are shut in order to ensure that the sample will remain inside the measuring element even after the latter is discarded. In this way the operating personnel is reliably protected against contact with the sample.

In a preferred variant of the invention it is provided that a buffer tank be added in the area of the first opening, and that the first sealing element have at least one further position, in which the measuring channel is connected with the buffer tank.

The invention further relates to a measuring element comprising a measuring channel with at least one optical or electrochemical sensor located therein, a first opening on one end of the measuring channel for connection of an analyser, and a second opening on the other end of the measuring channel for connection of a sample-taking part. This measuring element is characterised by the use of one common sealing element for both openings, which has three positions, the first position of this sealing element closing the measuring channel on both ends, the second position connecting one end of the measuring channel to the first opening and the other end of the measuring channel to a collecting tank provided in the measuring element, and the third position of the sealing element connecting one end of the measuring channel to a buffer tank provided in the measuring element and the other end of the measuring channel to the second opening. Manufacture and operation of the measuring element are simplified by providing only a single sliding element for establishing the desired connection. The measuring channel is essentially U-shaped, such that the two ends of the measuring channel are situated next to each other.

To prevent the analyser from being contaminated by the sample it is provided that any sample surplus be drained into the buffer tank. In the additional position of the first sealing element a suitable connection between measuring channel and first opening may be established in addition to the connection of the measuring channel to the buffer tank, through which the measuring channel may be evacuated. This connection is designed in such a way as to be impassable for the sample. It is also possible, however, to apply the vacuum immediately after calibration in the position of the first sealing element in which the measuring channel is connected to the first opening.

It is a special advantage if the sealing elements are configured as sliding elements, which slide in bores of the measuring element and are movable essentially at right angles to its longitudinal axis, or if the sealing elements are configured as rotary valves, which may be rotated in bores of the measuring element but cannot be shifted axially. In either instance both the slides, or valves, and the entire measuring element may be produced at low cost, which is of particular importance in the manufacture of single-use elements.

A variant of the invention provides that the joint sealing element be configured as a sliding element which is shifted in a guide of the measuring element, this sliding element being provided with a collecting tank preferably acting as a buffer tank at the same time.

Another advantage of this variant is that the sliding elements can be actuated automatically by corresponding pins of a suitable analyser. The passages in the sliding elements for establishing the corresponding connections are situated on different levels one above the other.

The collecting tank may have a variable volume or be provided with an exterior vent, preferably.

If the measuring channel is configured as a flat capillary only a minimum of sample material will be required for analysis.

In the invention the one-way measuring element may be provided with electric contact surfaces on its outer surface, which are connected to electrochemical sensors or a thermometer element in the measuring channel.

It is provided in a further variant of the invention that the measuring channel have a temperature sensor responding to any changes in temperature by a change in its optical properties, preferably by a change in its fluorescence decay time.

While one-way measuring elements with optical sensors must include transparent components for light guidance, it may also be an advantage for measuring elements with electrochemical sensors to incorporate at least one optically transparent zone into the measuring channel for detecting intrinsic optical properties of the sample. In this case the measuring element can also be used for measuring the natural fluorescence, absorption, reflectivity or refractive index of the sample.

DESCRIPTION OF THE DRAWINGS

Following is a more detailed description of the invention as illustrated by the accompanying drawings, in which FIG. 17 shows a further variant of the measuring element disclosed by the invention, as a section along line XVII—XVII in FIG. 19, FIG. 18 a section along line XVIII—XVIII in FIG. 19, FIG. 19 a section along line XIX—XIX in FIG. 17, and FIG. 20 a section along line XX—XX in FIG. 19.

FIGS. 16aa-16da, or rather, 16ab-16db and 16ac-16dc also show the positions of the rotary valve 43 of the variant presented in FIGS. 17 to 20 during the individual phases of the process, i.e. as sections along lines XXIa—XXIa, or rather, XXIb—XXIb and XXIc—XXIc in FIG. 17.

DETAILED DESCRIPTION OF THE PREFERRED EMBODIMENTS

Figure 1:
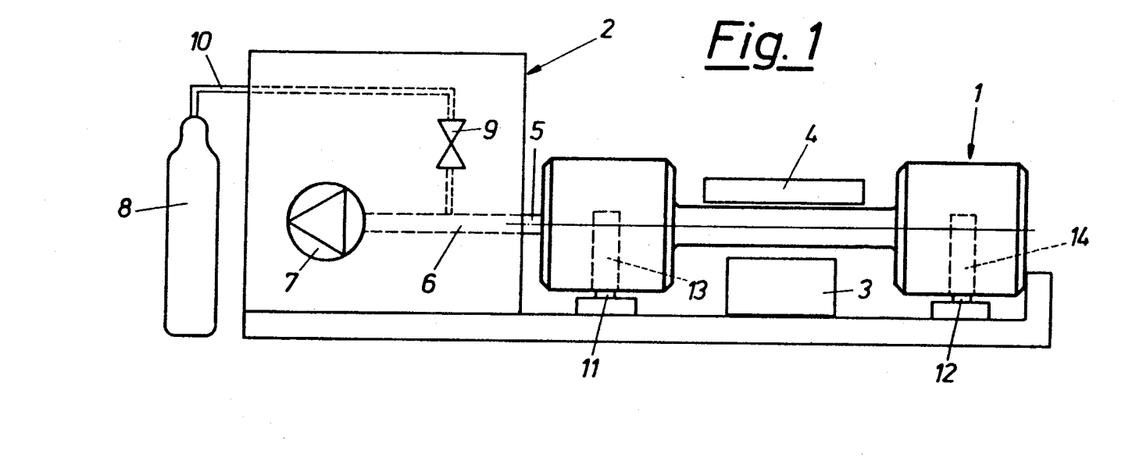
FIG. 1 is a schematic view of a measuring element as disclosed by the invention, connected to the analyzer, FIG. 2 a longitudinal section along line II—II in FIG. 3, FIG. 3 a view of the lower half of the measuring device, FIG. 4 a section along line IV—IV in FIG. 2, FIG. 5 a section of the first sliding element along line V—V in FIG. 6, FIG. 6 a section along line VI—VI in FIG. 5, FIG. 7 a section of the measuring element along line VII—VII in FIG. 2, FIG. 8 a section of the second sliding element along line VIII—VIII in FIG. 9, FIG. 9 a section along line IX—IX in FIG. 8, FIG. 10 a section of the measuring element along line X—X in FIG. 3, FIGS. 11a to 11d are views of the measuring element of the invention according to FIG. 3, corresponding to individual phases of the process.

As is shown in FIG. 1, a measuring element 1 is connected to and held by an analyser 2. The analyser 2 is provided with an optical assembly 3 for performing the required measurements. A temperature control 4 is provided to set a precisely defined temperature in the measuring zone. Via a fitting 5 and a pipe 6 a pump 7 in the analyser 2 is connected with the measuring element 1. The calibrating medium is taken from a gas reservoir 8 and fed into pipe 6 through a pipe 10 provided with a valve 9. The analyser 2 is further provided with pins 11 and 12 which are used for actuating the first sliding element 24 and the second sliding element 26.

Figure 2:
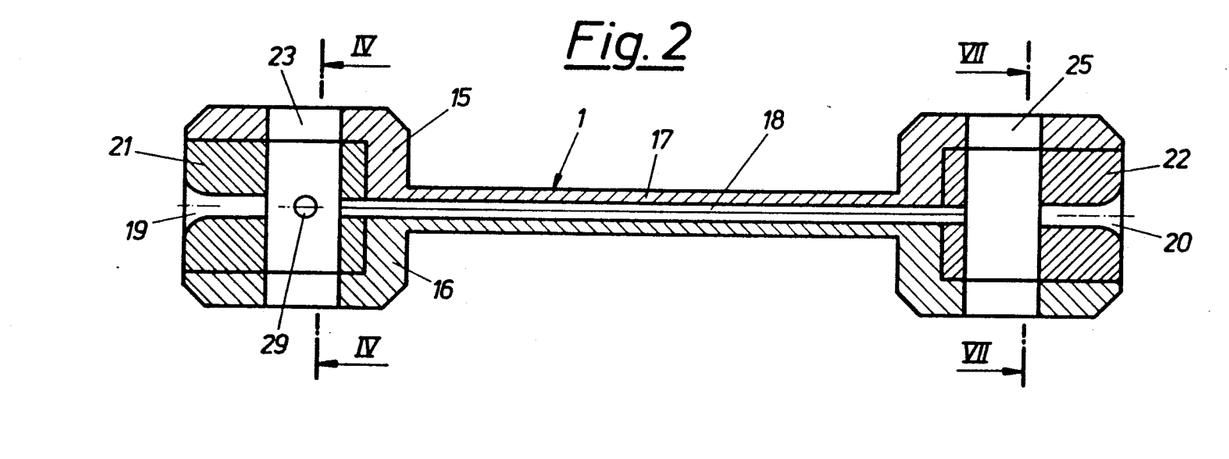
Figure 3:
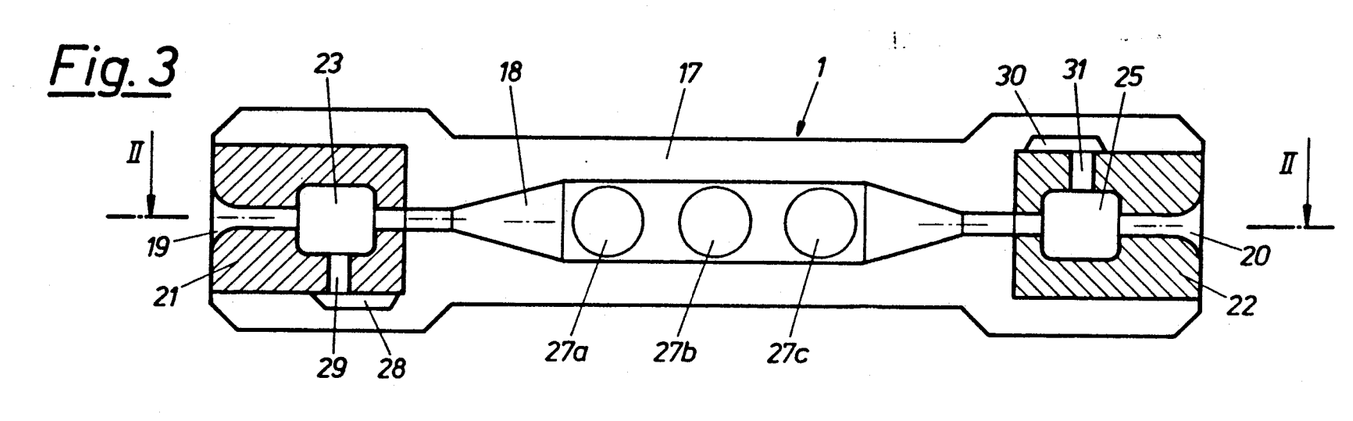
Figure 4:
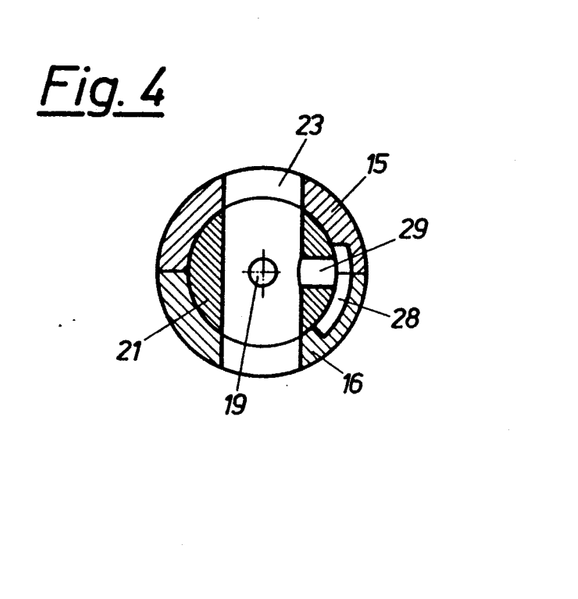

FIGS. 2 to 4 show that the measuring element 1 is composed of an upper housing part 15 and a lower housing part 16. For ease of manufacture the two parts 15 and 16 preferably are identical. The measuring element 1 has a central part 17 containing the measuring channel 18. The measuring element 1 is provided with a first opening 19 on one end and a second opening 20 on the other end for connection of the analyser 2 and the sample-taking part (not shown here). Coupling to the analyser and the sample-taking part is facilitated by the use of coupling elements 21, 22, which are inserted in suitable recesses at the ends of the measuring element 1.

The measuring channel 18 contains optical sensors 27a, 27b, 27c for sample analysis. Instead of these optical sensors electro-chemical sensors may be used, as is shown, for instance, in the variant presented in FIGS. 18 and 19. One of the optical sensors, e.g., 27c, may also be employed for temperature measurement, for example, with the use of an indicator whose fluorescence decay time is temperature-dependent.

In the area of opening 19 a first bore 23 is provided in which a first sliding element 24 can be shifted. The bore 23 crosses the measuring channel 18. In the area of opening 20 a second bore 25 is provided in which a sliding element 26 can be shifted. A buffer tank 28 in the area of the first opening 19 is connected on one side to the first bore 23 via a passage 29. A collecting tank 30 in the area of the second opening 20 is connected on one side to the second bore 25 via a passage 31.

Figure 5:
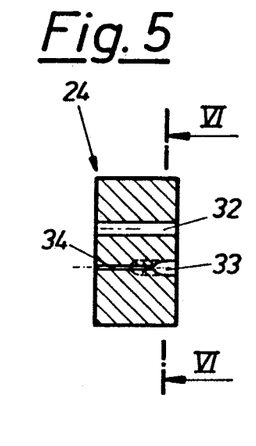
Figure 6:
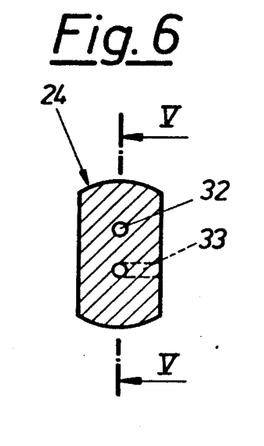
Figure 7:
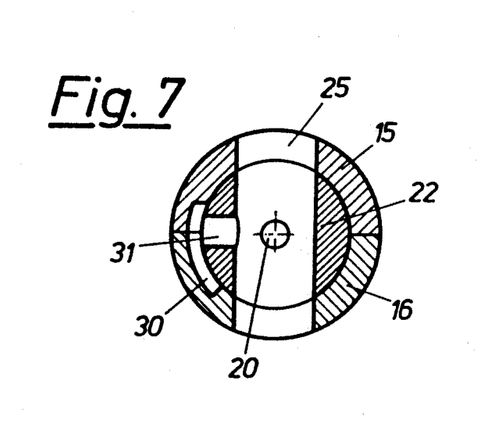

As is shown in FIGS. 5 and 6, the first sliding element 24 has a passage 32 which will connect the measuring channel 18 and the first opening 19 when the sliding element 24 is in suitable position. The sliding element 24 has a further passage 33 which will connect the measuring channel 18 and the buffer tank 28 when the sliding element 24 is in suitable position. Passage 33 is further connected with a thin suction passage 34 which may be used to establish a vacuum in the measuring channel 18 via opening 19.

Figure 8:
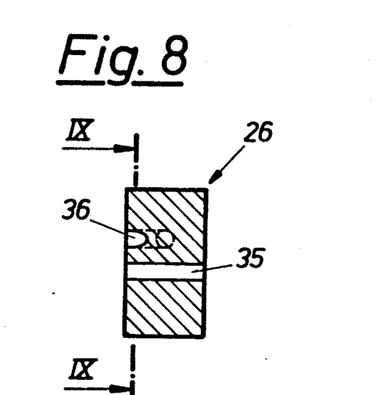
Figure 9:
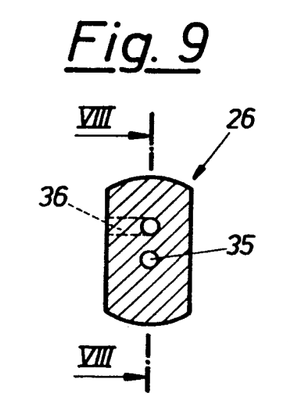
Figure 10:
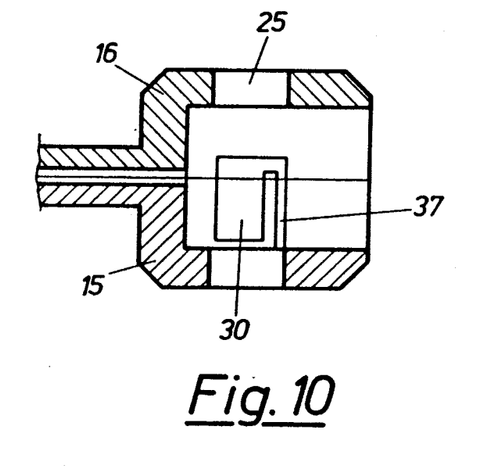

The sliding element 26 (FIGS. 8 and 9) has a passage 35 which will connect the measuring channel 18 and the second opening 20 when the sliding element 26 is in suitable position. A further passage 36 will connect the measuring channel 18 and passage 31, and thus the collecting tank 30, in a different position of the sliding element 26. FIG. 10 shows the collecting tank 30 and its vent 37. If this vent 37 is given a suitable design the gaseous calibrating medium may escape while the storage liquid will remain in the collecting tank.

Figure 11A:
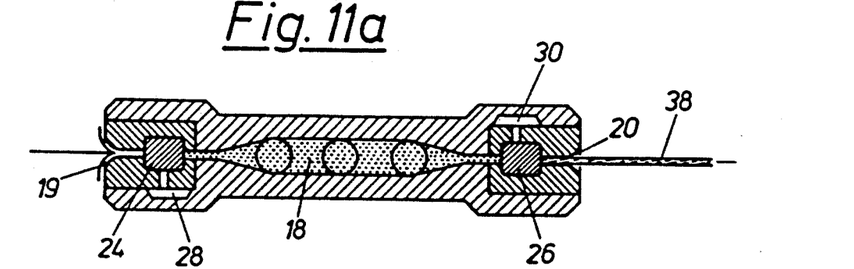
Figure 11B:
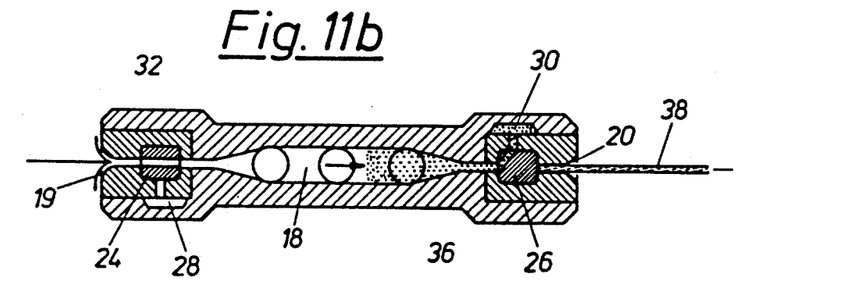
Figure 11C:
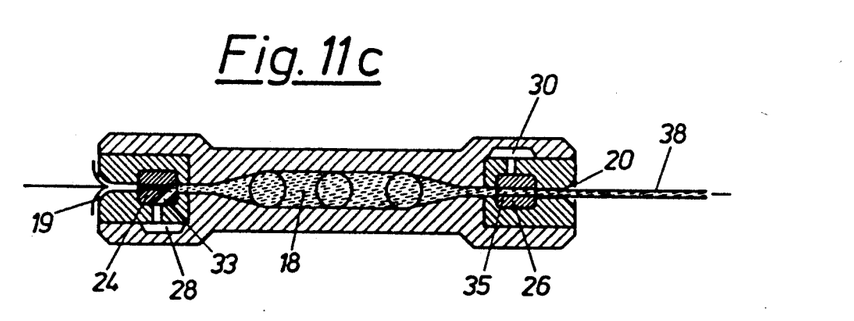

Following is a detailed functional description of the measuring element 1 as presented in FIGS. 11a to 11d. FIG. 11a shows the measuring element 1 in its state of delivery and storage. The measuring channel 18 is filled with the storage medium, the first sliding element 24 and the second sliding element 26 are closed. After connection of the measuring element 1 to the analyser 2 and the sample-taking part the first sliding element 24 is brought into a position in which its passage 32 will connect the measuring channel 18 and the first opening 19 (FIG. 11b). The second sliding element 26 is brought into a position in which its passage 36 will connect the measuring channel 18 of the measuring element 1 and the collecting tank 30. By introducing the calibrating medium or air through the opening 19 the storage medium is pushed out of the measuring channel 18 and collected in the collecting tank 30. The calibrating gas will escape through vent 37, while the storage medium will remain in the collecting tank 30. At the end of the calibrating test the first sliding element 24 is adjusted to assume a position (FIG. 11c) in which its passage 33 will connect the measuring channel 18 of the measuring element 1 to the buffer tank 28. The suction passage 34 (FIG. 5) connects to the first opening 19. The second sliding element 26 is adjusted to assume a position in which its passage 35 will establish a connection between the measuring channel 18 and the second opening 20. In this position the analyser 2 will produce a vacuum in the measuring channel 18 of the measuring element 1 via the suction passage 34. As a result the sample to be analysed is sucked in from the sample-taking part 38 indicated schematically. Any sample surplus will be fed to the buffer tank 28 through the passage 33 of the first sliding element 24. Now the actual measuring process may be initiated.

Figure 11D:
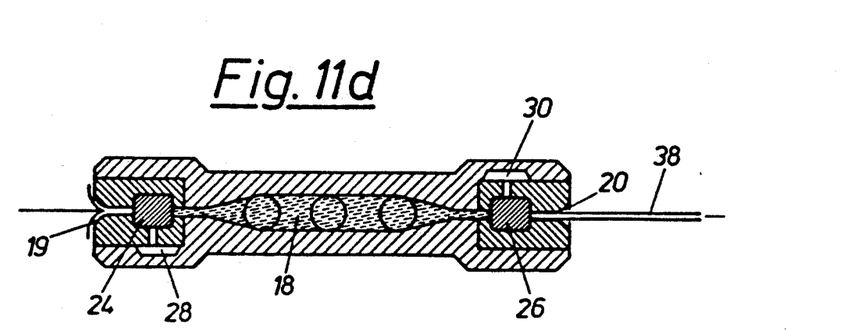
Figure 12:
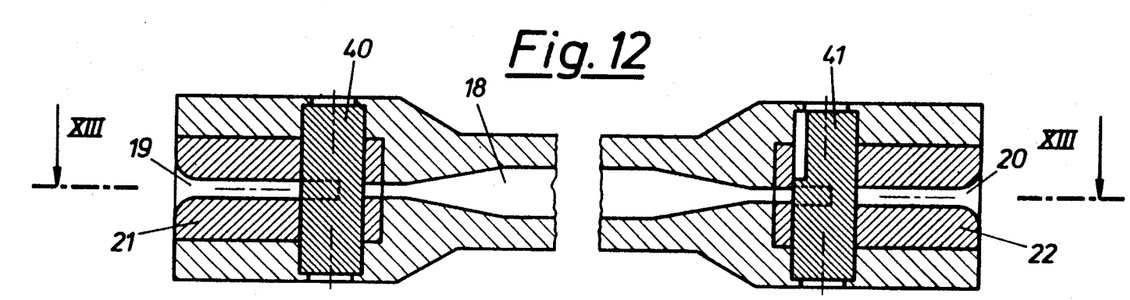
FIG. 12 is a section of the further variant of the measuring element of the invention, along line XII—XII in FIG. 13, FIG. 13 a section along line XIII—XIII in FIG. 12, FIG. 14 a section along line XIV—XIV in FIG. 13, FIG. 15 a section along line XV—XV in FIG. 13, FIGS. 16a to 16dc show the positions of the individual rotary valves of the variant presented in FIGS. 12 to 15, during the individual phases of the process.
Figures 13, 14, 15:
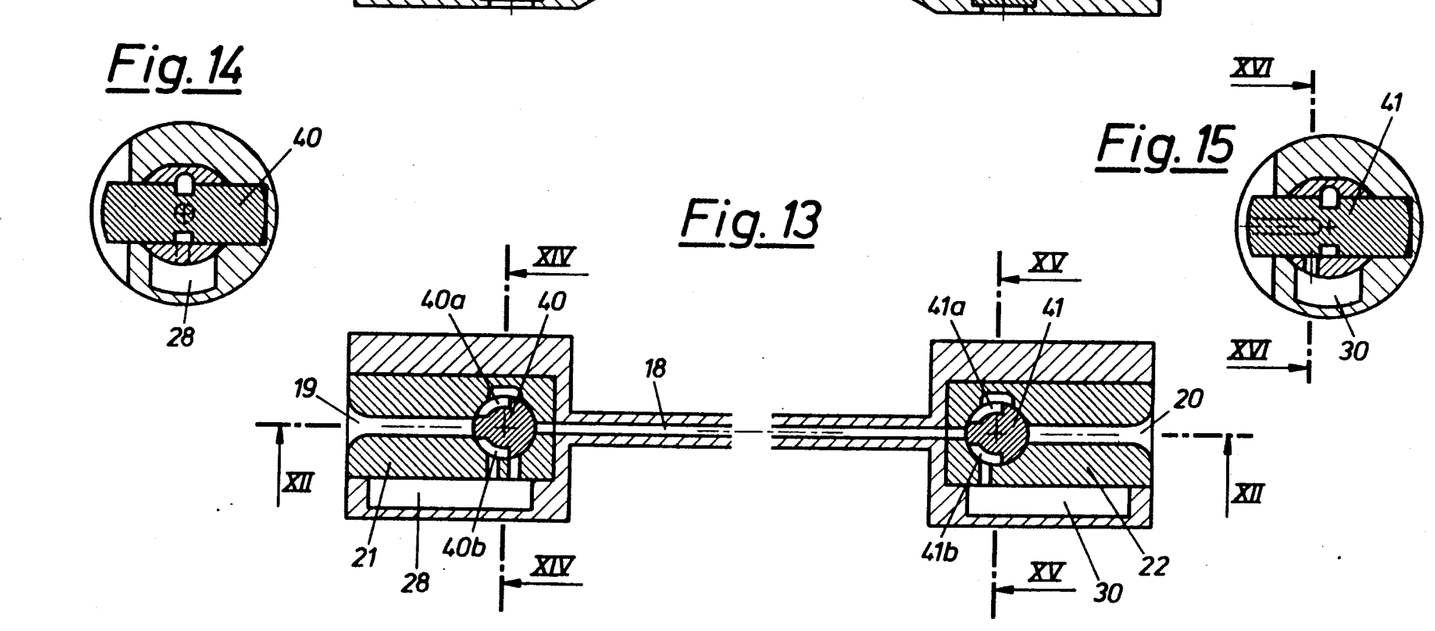

At the end of the measuring process the first sliding element 24 and the second sliding element 26 are brought into another position (FIG. 11d), in which they close off the measuring channel 18 on both ends. In this position the measuring element 1 may be decoupled from the analyser 2 and the sample-taking part 38 and may then be discarded.

The measuring element shown in FIGS. 12 to 15 is provided with rotary valves 40 and 41, which are located on either end of the measuring channel 18 such that they may be rotated but cannot be shifted axially. The rotary valves 40 and 41 have recesses 40a, 40b, 41a, 41b, which will establish a connection or separation between the measuring channel 18 and the first opening 19 or the second opening 20, or the buffer tank 28 or the collecting tank 30, depending on the respective positions of the rotary valves 40 and 41.

Figure 16:
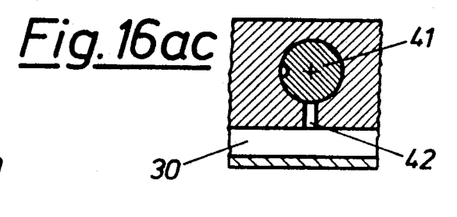

FIGS. 16aa to 16dc show the positions of the rotary valves 40 and 41 during the individual phases of the procedure, FIGS. 16aa–16ac corresponding to the storage/transport position, FIGS. 16ba–16bc to the position in which the storage medium may be displaced by the calibrating medium, FIGS. 16ca–16cc to the position in which the sample is drawn in, and FIGS. 16da–16dc to the position in which the measuring element may be discarded. FIGS. 16ac–16dc correspond to a section along line XVI—XVI in FIG. 15. FIGS. 16aa to 16ac show that both ends of the measuring channel 18 are closed off. Thus the storage medium cannot be lost. In FIGS. 16ba to 16bc the rotary valve 40 is rotated clockwise by 90°, and valve 41 counterclockwise by 90°. In this position the storage medium can be pushed into the collecting tank 30 by the calibrating medium. Bore 42 is used for venting the collecting tank 30.

In FIGS. 16ca to 16cc the rotary valves 40 and 41 are rotated by 180° vis-a-vis their previous position. Now the sample can be sucked into the measuring channel 18 while the calibrating medium is sucked into the buffer tank 28.

In FIGS. 16da to 16dc the initial position of the rotary valves 40 and 41 is reached once again, preventing the sample from leaving the measuring channel and permitting safe disposal of the measuring element.

Figures 17, 18, 19:
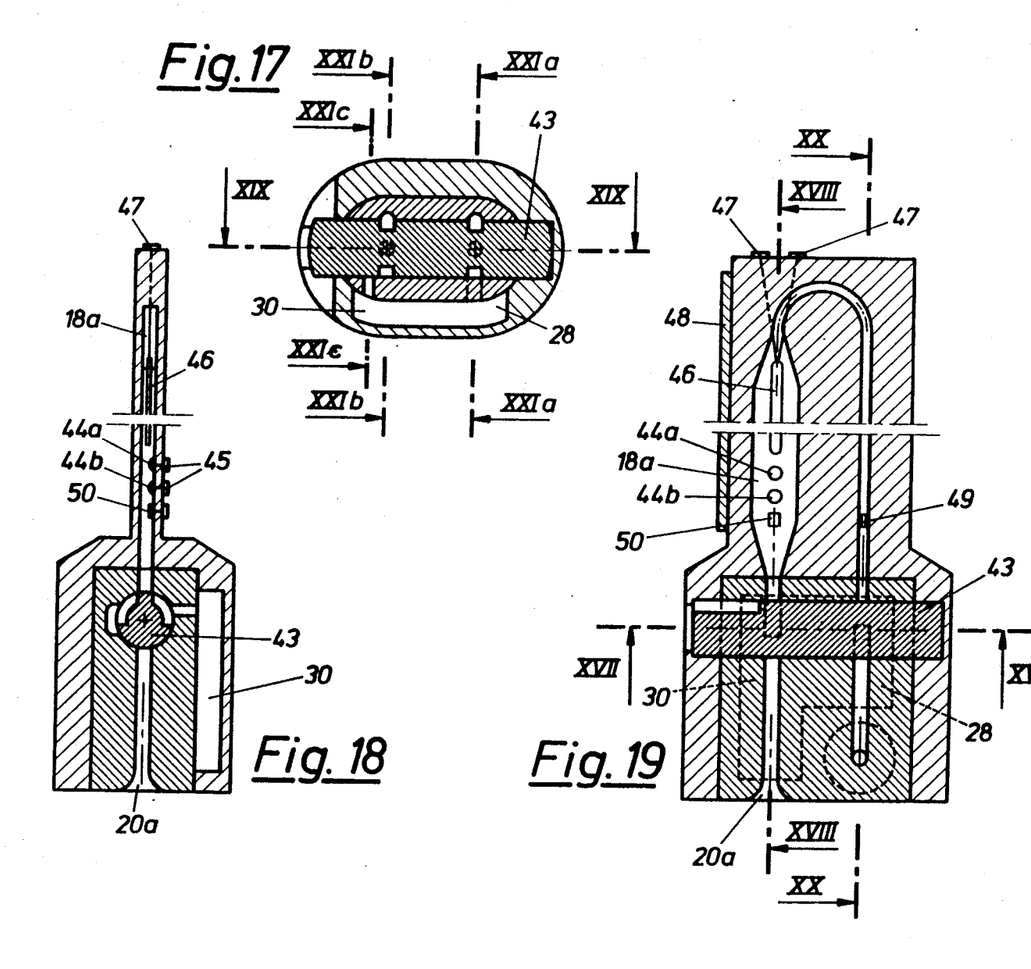
Figure 20:
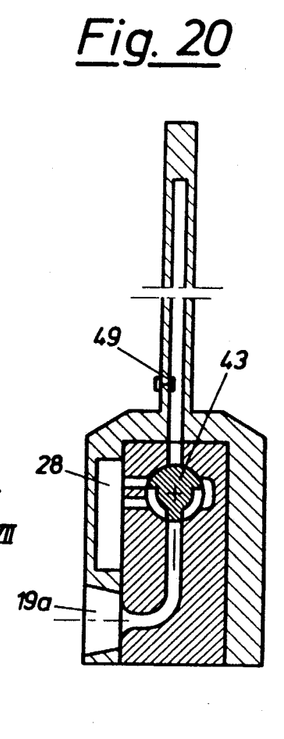

In the variant of the invention shown in FIGS. 17 to 20 a single rotary valve 43 is provided. As the measuring channel 18a is U-shaped in this instance, both the first opening 19a and the second opening 20a are situated on the same side of the measuring element. In this variant the rotary valve 43 performs both the task of the rotary valve 40 and that of the rotary valve 41 of the variant presented in FIGS. 12 to 15. The section along line XXIa—XXIa in FIG. 17 corresponds to FIGS. 16ab–16dc, and the section along line XXIb—XXIb in FIG. 17 to FIGS. 16ab–16db, and the section along line XXIc—XXIc in FIG. 17 to FIGS. 16ac–16dc. For details of this variant please compare the description of FIG. 16. As is seen in FIG. 19, the collecting tank 30 and the buffer tank 28 may be one and the same in this variant.

As is shown in the variant of FIGS. 17 to 20, it is also possible to provide electrochemical sensors 44a, 44b in the measuring channel 18, which are contacted via electrical contact surfaces 45 on the outer surface of the measuring element.

It is further possible to provide a thermometer element 46 in the measuring channel 18a, whose signals may be read via contact surfaces 47 when the measuring element is inserted into an analyser as in FIG. 1. The same applies to a device for determining conductivity, with electrodes 49, 50 dipping into the measuring channel 18a.

Finally, data such as the date of manufacture, number of sensors, sensor characteristics, or the measuring sensitivity of the one-way measuring element may be recorded using a magnetic code or bar code or a memory chip 48 to be read by the analyser.

It is of course also possible to use optical sensors in this variant, or electrochemical sensors, temperature measuring devices and coding elements in the previous variants.

Figure 21:
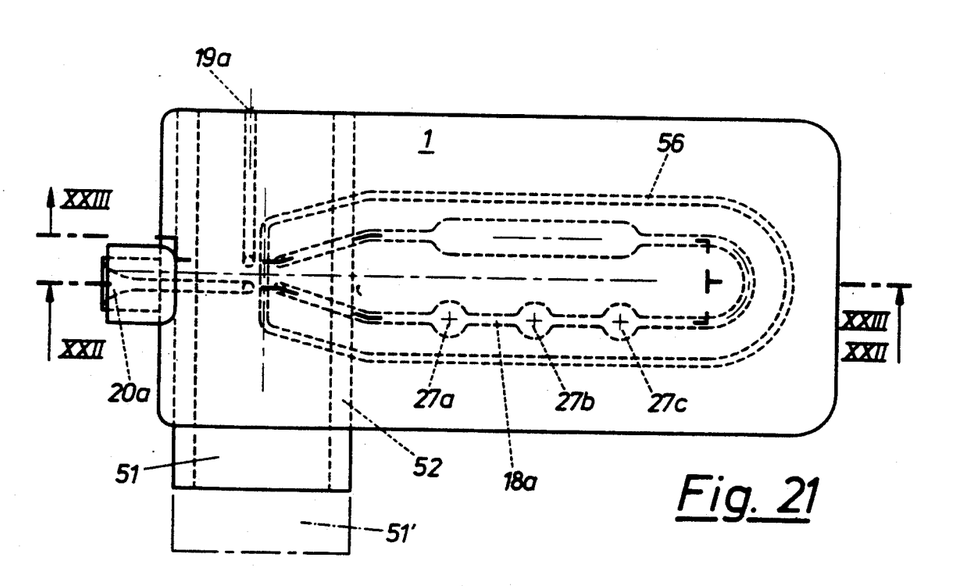
FIG. 21 is a view from above of a further variant of a measuring element as disclosed by the invention, FIG. 22 a section along line XXII—XXII in FIG. 21, and FIG. 23 a section along line XXIII—XXIII in FIG. 21.
Figure 22:
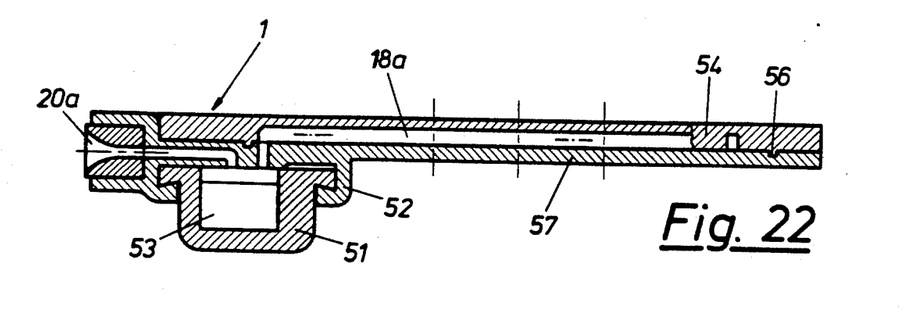
Figure 23:
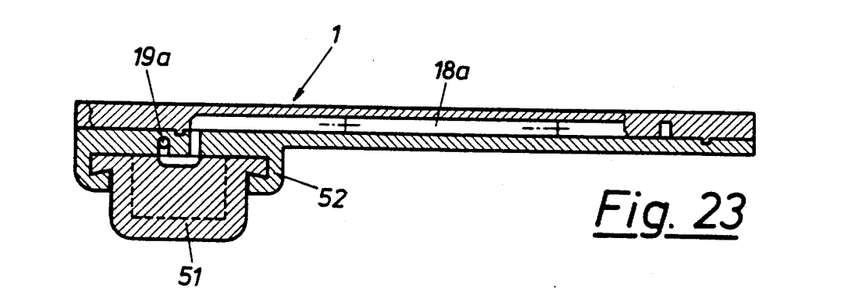

In the variant of the invention presented in FIGS. 21 to 23 a single sliding element 51 is provided, which can be shifted in a guide 52 of the measuring element 1. Again, the measuring channel 18a is essentially U-shaped, and both openings 19a and 20a can be served by one sealing element. The sliding element 51 (a further slide position is marked 51') performs both the tasks of sliding element 24 and those of sliding element 26, as presented in FIGS. 11a–11d. In this variant the collecting tank in 53 is located in the sliding element 51 where it also serves as a buffer tank.

Preferably, the measuring element is cconfigured as a two-part element, in which the upper part 54 of FIG. 22 has a ridge 55 engaging in a continuous groove 56 along the lower part 57 upon assembly.

In FIGS. 22 and 23 the sliding element 51 is presented in a position in which the measuring channel 18a of the measuring element can be filled with a storage medium.

We claim:

1. One-way measuring element comprising a measuring channel with at least one optical or electrochemical sensor located therein, a collecting tank provided in said measuring element, a first opening on a first end of said measuring channel for connecting said measuring element to an analyser, and a second opening on a second end of said measuring channel for connecting said measuring element to a sample-taking part, wherein one common sealing element is used for both of said first and second openings which has first, second and third positions, said first position of said sealing element closing said measuring channel on both of said first and second ends, said second position connecting said first end of said measuring channel to said first opening and said second end of said measuring channel to said collecting tank, and said third position of said sealing element connecting said first end of said measuring channel to a said collecting tank and said second end of said measuring channel to said second opening.

2. Measuring element according to claim 1, wherein said common sealing element is configured as a sliding element, which is shifted in a guide of said measuring element.

3. Measuring element according to claim 2, wherein said common sliding element is provided with a collecting tank.

4. Measuring element according to claim 1, wherein said common sealing element is configured as a rotary valve which may be rotated in bores of said measuring element but cannot be shifted axially.

5. Measuring element according to claim 1, wherein said collecting tank has a vent.

6. Measuring element according to claim 1, wherein said measuring channel is configured as a flat capillary.

7. Measuring element according to claim 1, wherein electric contact surfaces are provided on the outer surface of said measuring element, which are connected to electrochemical sensors in said measuring channel.

8. Measuring element according to claim 1, wherein electric contact surfaces are provided on the outer surface of said measuring element, which are connected to a thermometer element in said measuring channel.

9. Measuring element according to claim 1, wherein said measuring channel comprises a temperature sensor responding to a change in temperature by a change in its optical properties.

10. Measuring element according to claim 9, wherein said temperature sensor measures a change in fluorescence decay time.

11. Measuring element according to claim 1, wherein electrodes of a device for determining conductivity dip into said measuring channel.

12. Measuring element according to claim 1, wherein the outer surface of said measuring element is provided with a magnetic code or bar code or a memory chip.

13. Measuring element according to claim 1, wherein said measuring channel has at least one optically transparent zone for detecting intrinsic optical properties of said gaseous or liquid sample.

14. Measuring element according to claim 1, wherein said measuring channel is U-shaped.

15. One-way measuring element comprising a measuring channel with at least one optical or electrochemical sensor located therein, a collecting tank provided in said measuring element, a first opening on a first end of said measuring channel for connecting said measuring element to an analyser, and a second opening on a second end of said measuring channel for connecting said measuring element to a sample-taking part, wherein one common sealing element is used for both of said first and second openings which has at least first, second and third positions, said first position of said sealing element closing said measuring channel on both of said first and second ends, said second position connecting said first end of said measuring channel to said first opening and said second end of said measuring channel to said collecting tank, and said third position of said sealing element connecting said first end of said measuring channel to said collecting tank and said second end of said measuring channel to said second opening, and wherein said collecting tank has a vent.

* * * * *

UNITED STATES PATENT AND TRADEMARK OFFICE
CERTIFICATE OF CORRECTION

PATENT NO. : 5,228,350
DATED : July 20, 1993
INVENTOR(S) : Karpf et al

It is certified that error appears in the above-indentified patent and that said Letters Patent is hereby corrected as shown below:

On the title page: Item [75]

[75] Inventors: Hellfried Karpf; Marco Jean-Pierre Leiner; Anton Möstl, all of Graz; Klaus Reichenberger, Knittelfeld; Bernard Schaffar; Werner E. Ziegler, both of Graz, all of Austria Signed and Sealed this Twenty-second Day of March, 1994

Attest:

BRUCE LEHMAN

Attesting Officer     Commissioner of Patents and Trademarks